United States Patent [19]

Teller et al.

[11] Patent Number: 4,634,789
[45] Date of Patent: * Jan. 6, 1987

[54] CONVERSION OF ACETONITRILE TO GLYCOLONITRILE AND/OR GLYCOLAMIDE

[75] Inventors: Raymond G. Teller, Aurora; James F. Brazdil, Mayfield Village; Linda C. Glaeser, Middleburg Heights, all of Ohio

[73] Assignee: The Standard Oil Company, Cleveland, Ohio

[*] Notice: The portion of the term of this patent subsequent to May 7, 2002 has been disclaimed.

[21] Appl. No.: 643,207

[22] Filed: Aug. 22, 1984

[51] Int. Cl.$^4$ .................. C07C 121/34; C07C 121/36; C07C 102/08
[52] U.S. Cl. ..................................... 558/451; 558/457
[58] Field of Search ..................... 260/465.6; 564/130; 558/451

[56] References Cited

U.S. PATENT DOCUMENTS 3,516,789  6/1970  Sennewald et al. ......... 260/465.3 X
4,515,732  5/1985  Brazdil et al. .................... 260/465.6

OTHER PUBLICATIONS

Deutsch et al.; J. Prabst. Chemie, 321(1), (1979), pp. 137–140.

*Primary Examiner*—Joseph Paul Brust
*Attorney, Agent, or Firm*—Charles S. Lynch; John E. Miller; Larry W. Evans

[57] ABSTRACT

The vapor phase oxidation of acetonitrile with molecular oxygen in the presence or absence of water vapor to produce glycolonitrile or glycolamide in the presence of a vanadium oxide based catalyst.

10 Claims, No Drawings

CONVERSION OF ACETONITRILE TO GLYCOLONITRILE AND/OR GLYCOLAMIDE

This invention relates to a novel catalytic method of making glycolonitrile and/or glycolamide from acetonitrile.

The conventional method to prepare glycolonitrile has been by the reaction of formaldehyde with either hydrocyanic acid or with a mixture of water and sodium cyanide. Glycolonitrile can be hydrolyzed to glycolamide. Because of the relatively dangerous nature of inorganic cyanides, it is desirable to avoid such starting material reactants. Moreover, acetonitrile is a product which is available in fairly large quantities as a by-product from other processes and it is of rather low value, and is thus an inexpensive starting material.

It is an object of the present invention to provide a new catalytic method for making glycolonitrile and/or glycolamide that does not utilize inorganic cyanides.

It is a further object of the present invention to provide a catalytic process for making glycolonitrile and/or glycolamide from acetonitrile.

Other objects, as well as aspects and advantages, of the invention will become aparent from a study of the specification and claims.

The foregoing objectives are realized by the present invention according to which there is provided a catalytic process for making glycolonitrile or glycolamide which comprises the vapor phase oxidatin of acetonitrile with molecular oxygen in the presence or absence of water vapor and in the presence of a solid vanadium oxide based catalyst having the elements and the proportions indicated by the following empirical formula:

$$A_a B_b V_c O_x$$

where
A is one or more of K, Na, Rb, Cs, Tl, Mg, Ca, Li;
B is one or more of Ti, Cr, Mn, Fe, Co, Ni, Cu, Ag, Zn, Au, Zr, Nb, Mo, Ta, W, Th, La Ce, Pr, Nd, Sm, Eu, Sb, Te, and Sn
a=0-2, usually 0-1,
b=0-3, usually 0-1,
c=2-15,
c≧(a+b) and
x is determined by the oxidaton state of the other elements present.

When effected in the presence of water either or both of glycolamide and glycolonitrile is formed in a single step.

In the foregoing process an especially useful group of catalysts are vanadium oxide based catalysts having the elements and the proportions indicated by the following empirical formula:

$$A_a B_b V_c O_x$$

where
A is one or more of K, Cs, and Mg;
B is one or more of Ti, Cr, Fe and Cu;
a=0-2, usually 0-1;
b=0-3, usually 0-1;
c=2-15;
c≧(a+b) and
x is determined by the oxidation state of the other elements present.

The catalysts can be on an inorganic oxide support such as alumina, silica, silica-alumina, etc. with the support being 5-95, usually 10-90 weight percent of the catalyst composition.

Especially useful catalysts are where A is K, a is 0.005-0.05, b is zero and c is 2; and where B is Fe, a is zero, b is 0.05-0.5 and c is 2.

It should be understood that the valence state of the vanadium or other metals in the active catalyst during the catalytic reaction is not known.

The overall reaction going from acetonitrile to glycolonitrile or glycolamide (or both) requires one half mole of molecular oxygen gas. However, according to the invention it is contemplated that a deficiency of oxygen can be employed, as little as, for instance, one tenth mole per mole of acetonitrile, with unreacted acetonitrile being available for recycle. Usually no more than two moles of molecular oxygen are employed for each mole of acetonitrile, although higher ratios can be employed.

The reaction is effected at temperatures between 200° and 700° C., usually between 250° and 550° C. The gaseous molecular oxygen can of course be diluted with a nonreactive gas such as nitrogen; in this connection, air can of course be used. The reaction is effected by contacting the reactants with the solid heterogeneous vanadium oxidation catalyst, and can be carried out in a fixed bed, fluid bed, transfer line or a gravitating moving bed reactor. Reactor pressures are not critical and can be well below or well above atmospheric, but absolute pressures of 10 to 20 psi are usually empoyed.

It is a feature of the invention that one or both of fumaronitrile or maleonitrile are sometimes co-produced with the glycolonitrile and these useful products can be recovered and sold as such or converted to the corresponding diacids.

The following specific examples are illustrative only and demonstrate (1) the preparation of specific catalysts useful in the claimed process as well as (2) representative examples of the catalytic oxidation process of the present invention.

EXAMPLE 1

At low heat, ammonium metavanadate was dissolved in about 600 ml. of water. The temperature was raised to drive off water while stirring. It was dried at 120° C. overnight. It was then denitrified at 290° C. for 3 hours and then 425° C. for 3 hours. It was slurried in 300 ml. of water and placed in a 120° C. oven over the weekend. THe resulting dark blue $V_2O_5$ catalyst was ground to 20-35 mesh and then calcined at 550° C. for 3 hours prior to use.

EXAMPLE 2

$NH_4VO_3$ (116.99 g.) was stirred in about 300 ml. of distilled water with low heat. Silica sol (69.27 g. 40% $SiO_2$) was added. Cupric nitrate ($Cu(NO_3)_2$.(2.5 $H_2O$, 58.15 g.) was then added. The resulting slurry was heated and stirred to remove part of the water. It was then heated at 120° C. overnight to dry the solids. The dried material was then denitrified by heating at 290° C. for 3 hours, followed by 425° C. for 3 hours. It was ground to 20-35 mesh particle size. The catalyst was 80% $Cu_{0.5}V_2O_x$ on 20 percent $SiO_2$ support.

EXAMPLE 3

$NH_4VO_3$ (116.99 g.) was dissolved in about 600 ml. of distilled water. Silica sol (56.84 g. 40% $SiO_2$) was added. The resulting slurry was then heated and stirred to remove part of the water. It was dried by heating overnight at about 120° C. The catalyst was then denitrified and ground as in Example 2. This catalyst was 80% $V_2O_5$ on 20% $SiO_2$ support.

EXAMPLE 4

$NH_4VO_3$ (116.99 g.) was stirred in about 300 ml of distilled water with low heat. Silica sol (59.33 g. 40% $SiO_2$) was added. Ferric nitrate $(Fe(NO_3)_3$ 9 $H_2O$, 20.2 g.). was then added. The resulting slurry heated and stirred to remove part of the water. It was then heated at 120° C. overnight to dry the solids. The dried material was then denitrified by heating at 290° C. for 3 hours, followed by 425° C. for 3 hours. It was ground to 20–35 mesh particle size. This catalyst was 80% $Fe_{0.1}V_2O_x$ on 20 percent $SiO_2$ support.

EXAMPLE 5

$NH_4VO_3$ (116.99 g.) was stirred in about 300 ml of distilled water with low heat. Silica sol (56.94 g. 40% $SiO_2$) was added. Potassium nitrate ($KNO_3$) was then added. The resulting slurry heated and stirred to remove part of the water. It was then heated at 120° C. overnight to dry the solids. The dried material was then denitrified by heating at 290° C. for 3.5 hours, followed by 425° C. for 2.5 hours. It was ground to 20–35 mesh particle size. This catalyst was 80% $K_{0.01}V_2O_x$ on 20 percent $SiO_2$ support.

EXAMPLE 6

Ammonium vanadate ($NH_4VO_3$, 2.34 g) was stirred in about 50 ml. water. Particulate alumina (16.37 g.) was impregnated by about ¼ of the $NH_4VO_3$ solution for four times, drying being effected after each impregnation at 120° C. for periods of 4–16 hours. The final drying was overnight. The dried catalyst was denitrified as in Example 4. The catalyst was 10 precent $V_2O_5$ on 90 percent alumina support.

The following examples in Table 1 were effected in a tubular fixed bed reactor containing the solid granular catayst. The reactor was a stainless steel tube, and the catalyst was held in place by glass wool plugs. The tube was situated vertically between two halves of a thermostatically controlled heating block. The production was collected in an aqueous scrubber, and was analyzed for liquid products with high performance liquid chromatography and gas chromatograph. The gaseous effluent was also analyzed for $O_2$, $N_2$, CO and $CO_2$. The reaction conditions and results are given in Table 1.

without departing from the spirit and scope of the disclosure or from the scope of the claims.

We claim:

1. The production of glycolonitrile or glycolamide by the vapor phase oxidation of acetonitrile with molecular oxygen in the absence or presence of water vapor and in the presence of a vanadium oxide based catalyst having the elements and the proportions indicated by the following empirical formula:

$$A_aB_bV_cO_x$$

where

A is one or more of K, Na, Rb, Cs, Tl, Mg, Ca, Li;
B is one or more of Ti, Cr, Mn, Fe, Co, Ni, Cu, Ag, Zn, Au, Zr, Nb, Mo, Ta, W, Th, La Ce, Pr, Nd, Sm, Eu, Sb, Te, and Sn
a = 0–2
b = 0–3
c = 2–15,
c ≧ (a+b) and
x is determined by the oxidation state of the other elements present, wherein glycolamide is produced only when water is present.

2. The oxidation according to claim 1 wherein a=0–1 and b=0–1.

3. The vapor phase oxidation of claim 1 wherein the temperature of the oxidation reaction is in the range from 200° to 700° C.

4. The vapor phase oxidation of claim 1 wherein the temperature of the oxidation reaction is in the range from 250° to 550° C.

5. The production of glycolonitrile or glycolamide by the vapor phase oxidation of acetonitrile with molecular oxygen in the absence or presence of water vapor and in the presence of a vanadium oxide based catalyst having the elements and the proportions indicated by the following empirical formula:

$$A_aB_bV_cO_x$$

where

A is one or more of K, Cs, and Mg;
B is one or more of Ti, Cr, Fe and Cu;
a = 0–2
b = 0–3
c = 2–15;
c ≧ (a+b) and
x is determined by the oxidation state of the other elements present, wherein glycolamide is produced only when water is present.

6. The oxidation according to claim 5 wherein a=0–1 and b=0–1.

TABLE 1

| Example No. | Catalyst of Example | Temperature, °C. | Contact Time, Secs. | Mol Ratios $CH_3CN/O_2/N_2/H_2O$ | Acetonitrile Conversion, Percent | Yields, Percent | | Selectivities | |
|---|---|---|---|---|---|---|---|---|---|
| | | | | | | Glycolonitrile | Glycolamide | Glycolonitrile | Glycolamide |
| 8 | 1 | 375 | 0.21 | 1/0.51/10.7/1.34 | 6.54 | 0 | 4.21 | 0 | 64.3 |
| 9 | 2 | 350 | 0.11 | 1/0.6/10.5/1.3 | 16.1 | 4.65 | 0 | 29.0 | 0 |
| 10 | 3 | 300 | 1.3 | 1/0.6/11.4/1.3 | 26.4 | 6.8 | 0 | 25.6 | 0 |
| 11 | 4 | 350 | 0.11 | 1/0.6/10.5/1.3 | 11.1 | 0.4 | 5.55 | 3.64 | 50.2 |
| 12 | 5 | 375 | 0.15 | 1/0.5/10.1/1.3 | 12 | 0 | 4.10 | 0 | 34.1 |
| 13 | no catalyst | 375 | 0.15 | 1/0.5/10.1/1.3 | 0.04* | 0 | 0 | 0 | 0 |
| 14 | 6 | 300 | 0.14 | 1/0.7/13.2/1.3 | 9.9 | 0 | 4.52 | 0 | 45.7 |
| 15 | 3 | 375 | 0.15 | 1/0.6/11.4/1.3 | 8.7 | 0 | 4.9 | 0 | 56 |
| 16 | 4 | 375 | 0.11 | 1/0.53/10.83/0 | 28.3 | 1.82 | 0 | 6.42 | 0 |

*All converted to HCN

As will be evident to those skilled in the art, various modifications of this invention can be made or followed in the light of the foregoing disclosure and discussion 7. The vapor phase oxidation of claim 5 wherein the temperature of the oxidation reaction is in the range from 200° to 700° C.

8. The vapor phase oxidation of claim 5 wherein the temperature of the oxidation reaction is in the range from 250° to 550° C.

9. The oxidation of claim 5 wherein A is K, a is 0.005–0.05, b is zero and c is 2.

10. The oxidation of claim 5 wherein B is Fe, a is zero, b is 0.05–0.5 and c is 2.

* * * * *